US00PP35578P2

(12) United States Plant Patent
Hamilton et al.

(10) Patent No.: US PP35,578 P2
(45) Date of Patent: Jan. 16, 2024

(54) RASPBERRY PLANT NAMED 'DRISRASPTWENTYTHREE'

(50) Latin Name: ***Rubus idaeus* L.**
Varietal Denomination: DrisRaspTwentyThree

(71) Applicant: Driscoll's, Inc., Watsonville, CA (US)

(72) Inventors: Brian K. Hamilton, Watsonville, CA (US); Richard E. Harrison, Watsonville, CA (US); Thomas M. Sjulin, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/992,811

(22) Filed: Nov. 22, 2022

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./156, 203, 204
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Hamilton et al. |
| PP29,402 | P2 | 6/2018 | Vitten et al. |
| PP30,577 | P2 | 6/2019 | Vitten et al. |
| PP30,733 | P2 | 7/2019 | Hamilton et al. |
| PP31,850 | P2 | 6/2020 | Hamilton et al. |
| PP32,496 | P2 | 11/2020 | Vitten et al. |
| PP32,722 | P2 | 1/2021 | Vitten et al. |
| PP33,723 | P2 | 12/2021 | Vitten et al. |
| PP33,736 | P2 | 12/2021 | Vitten et al. |
| PP33,758 | P2 | 12/2021 | Vitten et al. |
| PP34,070 | P2 | 3/2022 | Vitten et al. |

OTHER PUBLICATIONS

Cousineau et al. (1992). "Use of Isoenzyme Analysis to Characterize Raspberry Cultivars and Detect Cultivar Mislabeling," HortScience, 27(9):1023-1025.

Williams et al. (1990). "DNA polymorphisms amplified by arbitrary primers are useful as genetic markers," Nucleic Acids Research, 18(22):6531-6535.

*Primary Examiner* — Susan McCormick Ewoldt
(74) *Attorney, Agent, or Firm* — Morrison & Foerster LLP

(57) ABSTRACT

A new and distinct variety of raspberry plant named 'DrisRaspTwentyThree', particularly selected for its machine harvestability, yield, flavor and fruit integrity during individual quick freeze (IQF) processing, is disclosed.

4 Drawing Sheets

Latin name:

Botanical classification: *Rubus idaeus* L.

Varietal denomination: The varietal denomination of the claimed variety of raspberry plant is 'DrisRaspTwentyThree'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*.

Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspTwentyThree'.

Raspberry plant variety 'DrisRaspTwentyThree' was selected in Whatcom County, Washington in July 2010 and originated from a controlled cross between the proprietary female parent 'W678.2' (unpatented) and the male parent 'Meeker' (unpatented). The original seedling of the new variety was first asexually propagated in Santa Cruz County, California via root cuttings in August 2010.

'DrisRaspTwentyThree' was subsequently asexually propagated via root cuttings, and has undergone testing in Whatcom County, Washington for ten years (2010 to 2020). The present variety has been found to be stable and reproduce true to type through successive asexual propagations via root cuttings.

'DrisRaspTwentyThree' was particularly selected for its machine harvestability, yield, flavor and fruit integrity during individual quick freeze (IQF) processing.

BRIEF DESCRIPTION OF THE DRAWINGS

This new raspberry plant is illustrated by the accompanying photographs. The colors shown are as true as can be reasonably obtained by conventional photographic procedures. The photographs are of plants that are two years old.

DETAILED BOTANICAL DESCRIPTION

Figure 1:
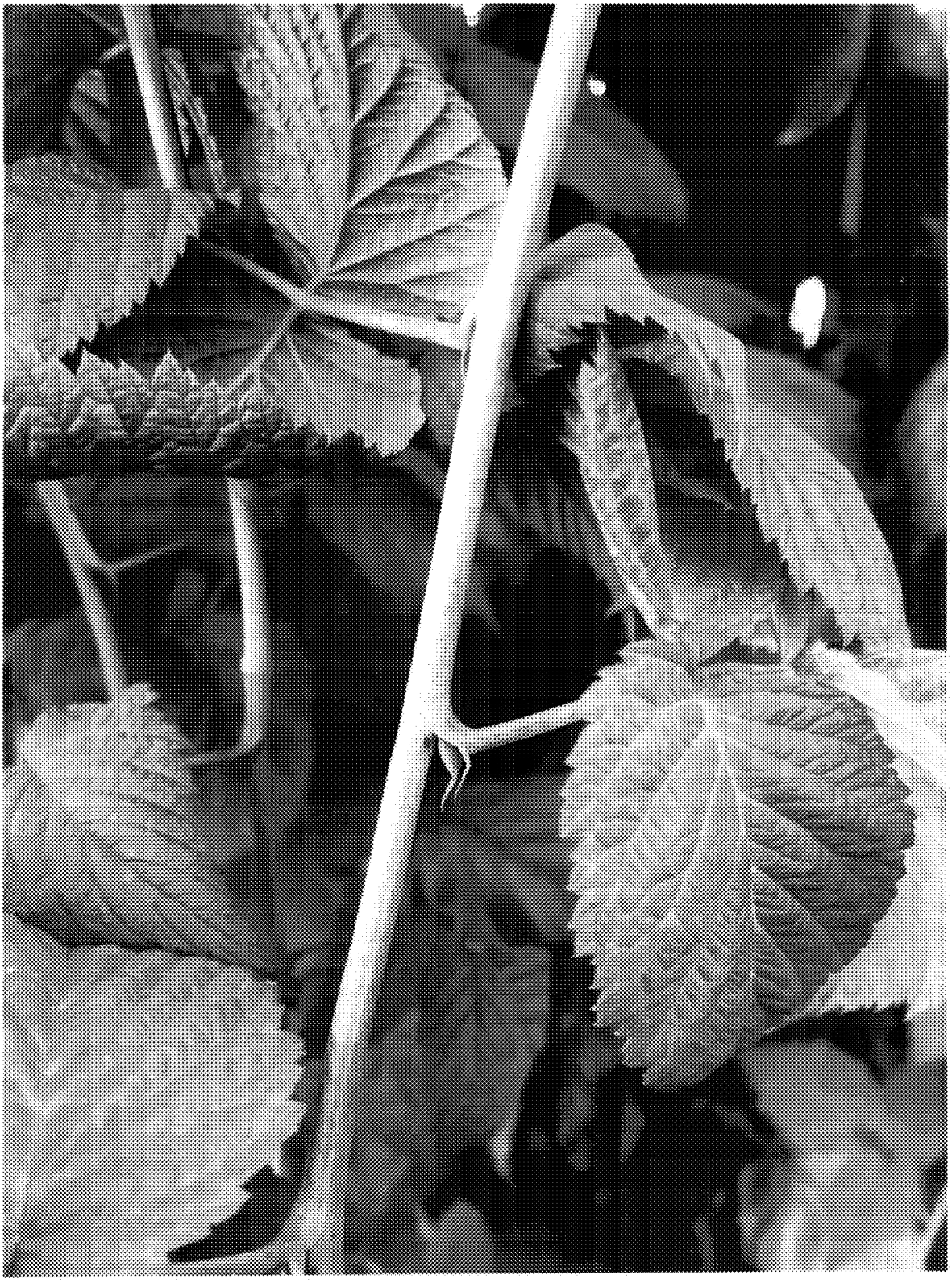
FIG. 1 illustrates a cane of raspberry variety 'DrisRaspTwentyThree'.
Figure 2:
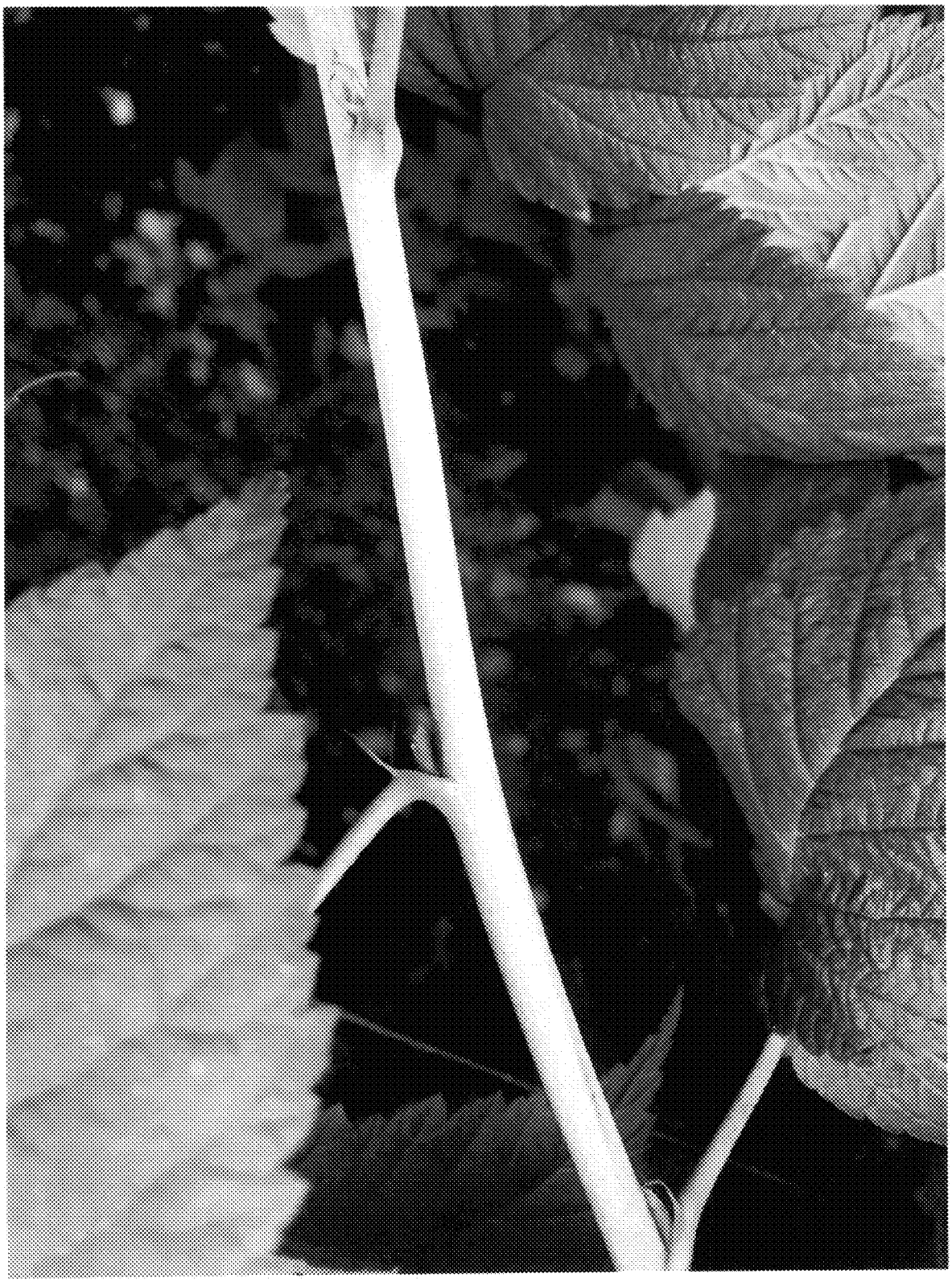
FIG. 2 illustrates another view of a cane of raspberry variety 'DrisRaspTwentyThree'.
Figure 3:
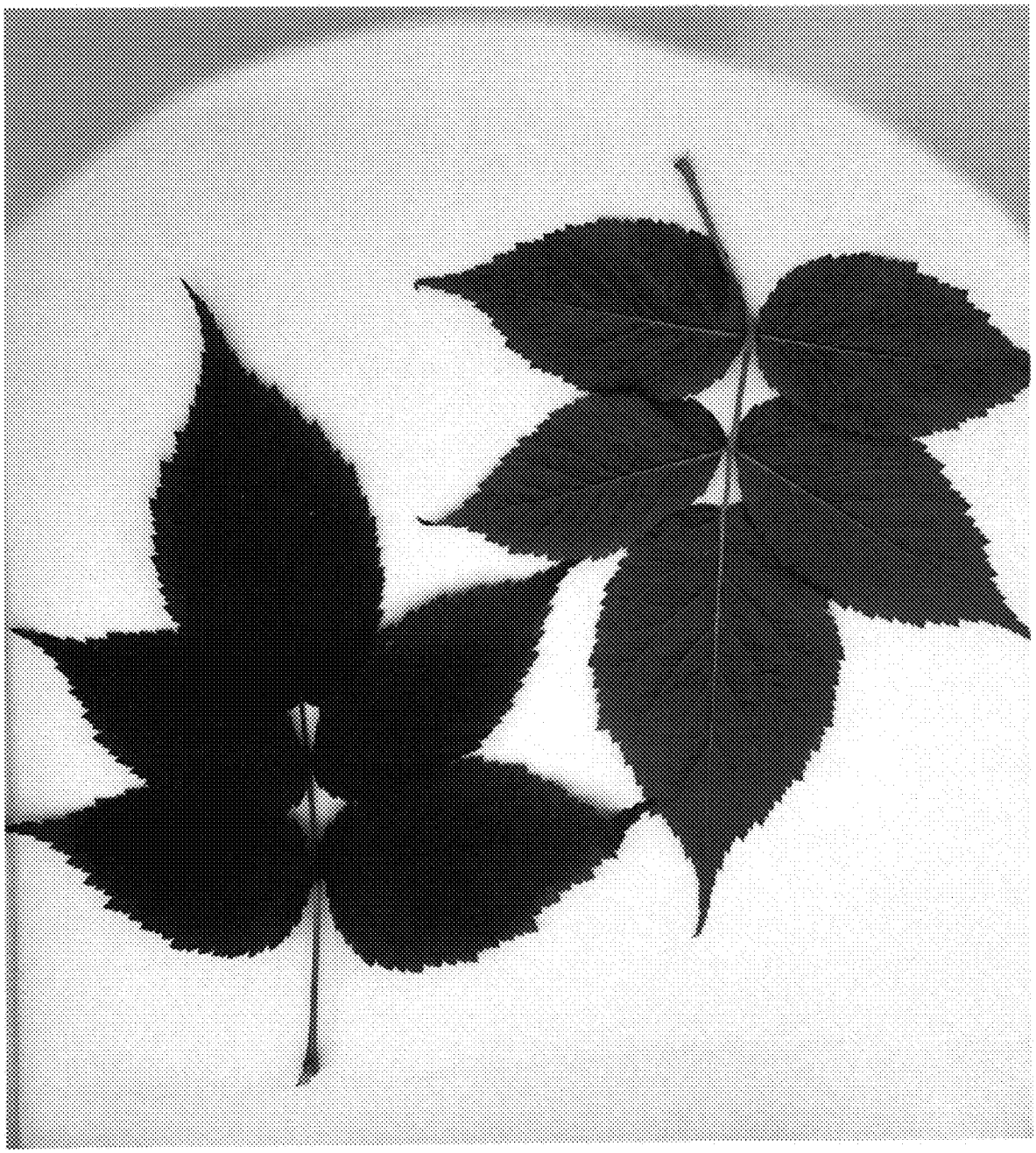
FIG. 3 illustrates the upper surface (left) and lower surface (right) of leaves of raspberry variety 'DrisRaspTwentyThree'.
Figure 4:
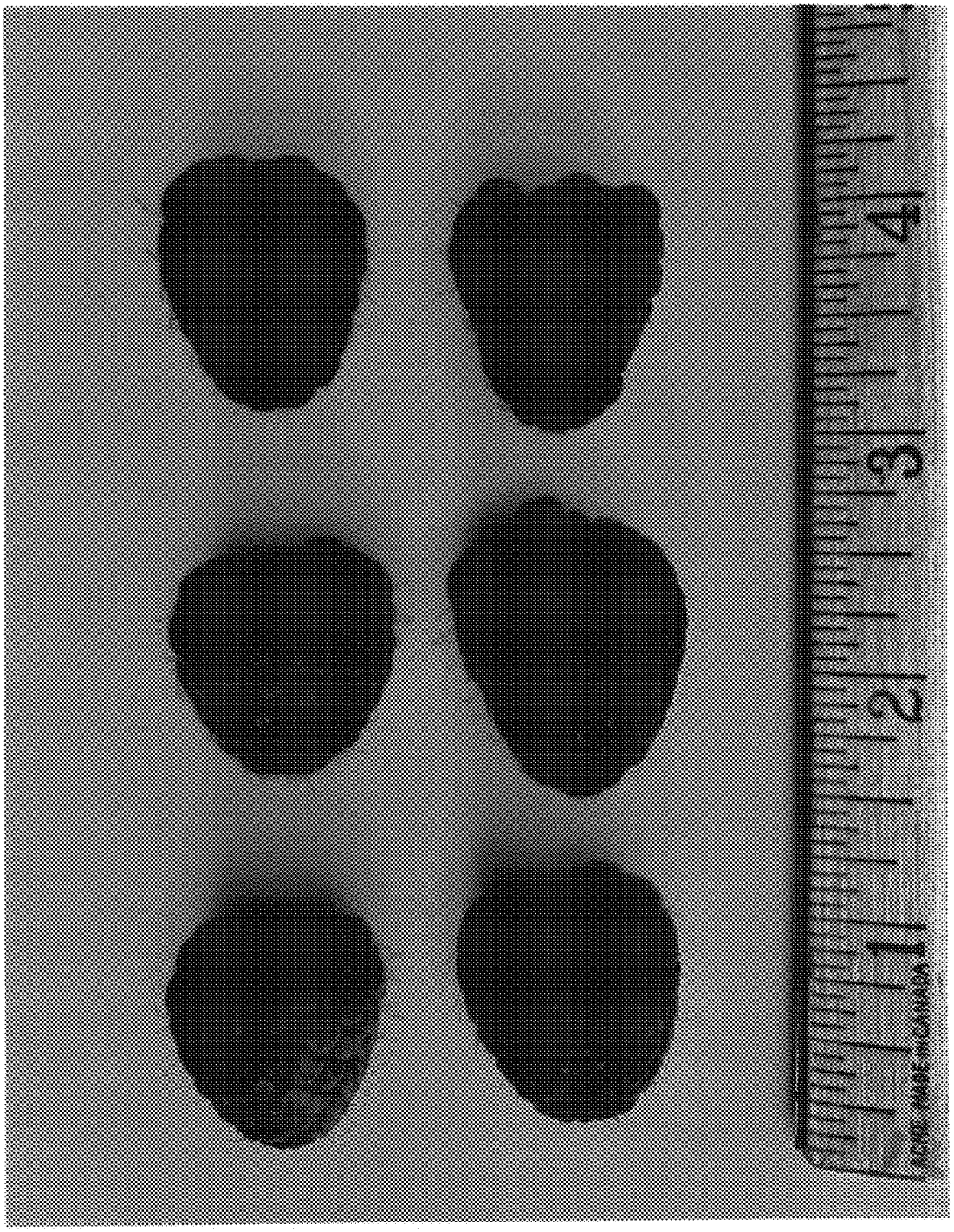
FIG. 4 illustrates mature fruit of raspberry variety 'DrisRaspTwentyThree'.

The following descriptions set forth the distinctive characteristics of 'DrisRaspTwentyThree'. Unless where otherwise noted, the data that define these characteristics are based on observations taken from 'DrisRaspTwentyThree' plants that were two years old, grown in Whatcom County, Washington from 2010 to 2020. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspTwentyThree' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.
*Botanical*.—*Rubus idaeus* L.
*Common name*.—Raspberry.
*Variety name*.—'DrisRaspTwentyThree'.

Parentage:

*Female parent*.—'W678.2' (unpatented).
*Male parent*.—'Meeker' (unpatented).

Plant:

*Height*.—418.8 cm.
*Width*.—139 cm.
*Length/width ratio*.—~3.
*Growth habit*.—Semi-upright.
*Primocane* (*current year's cane*).—Anthocyanin coloration of cane: Absent. Cane bloom: Absent or very weak. Internodal distance at central ⅓ of cane: 4.45 cm.
*Very young shoot*.—Anthocyanin coloration of apex during rapid growth: Absent. Color of young shoot: RHS 139C (Moderate yellow green).
*Dormant cane*.—Length: 304.8 cm. Color: Brownish purple (RHS 187C).
*Fruiting lateral*.—Attitude: Erect. Length: 40 cm.
*Prickles* (*spines*).—Presence: Absent.
*Plant main bearing type*.—Only on previous year's cane in summer.

Leaves:

*Predominant number of leaflets*.—Five.
*Profile of leaflets in cross section*.—Straight.
*Leaf rugosity*.—Weak.
*Color of upper side*.—Light green (RHS 141A).
*Color of lower side*.—RHS 139B (Moderate yellowish green).
*Shape of leaflet apex*.—Cuspidate.
*Shape of leaflet base*.—Cordate.
*Leaflet margin*.—Doubly serrate.
*Leaflet texture*.—Smooth.
*Venation pattern*.—Pinnate.
*Vein color*.—RHS 139D (Moderate yellow green).
*Terminal leaflet*.—Length: 101.9 mm. Width: 75.4 mm. Length/width ratio: 1.4.

*Lateral leaflets*.—Length: 166.8 mm. Width: 55.3 mm. Length/width ratio: 3.0. Relative position of lateral leaflets: Free.

*Rachis*.—Length between terminal leaflet and adjacent lateral leaflets: 26.9 mm. Color: RHS 139D (Moderate yellow green).

*Petiole*.—Length: 57.8 mm. Diameter: 2.72 mm. Color: RHS 145A (Strong yellow green).

Flowers:

*Diameter*.—30.23 mm.

*Petal*.—Length: 8.70 mm. Width: 4.07 mm. Length/width ratio: 2.1. Average number of petals per flower: 5. Color of upper surface: RHS NN155B (Yellowish white). Color of lower surface: RHS N155B (Yellowish white). Shape of base: Cuneate. Shape of apex: Cuspidate. Texture of upper surface: Smooth. Texture of lower surface: Smooth. Petal margin: Entire.

*Pedicel*.—Length: 49.20 mm. Diameter: 1.34 mm. Color: RHS 138B (Moderate yellow green). Number of spines: Absent or very few.

*Peduncle*.—Length: 18.97 mm. Diameter: 1.33 mm. Color: RHS 144B (Yellow green). Anthocyanin coloration: Absent.

*Reproductive organs*.—Stigma: Length: 2.8 mm. Width: 3.6 mm. Shape: Oblanceolate. Color: RHS NN155D (White). Anther: Length: 0.62 mm. Width: 0.41 mm. Shape: Oval. Color: RHS 166B (Moderate reddish brown). Pollen: Color: RHS NN155D (White).

Fruit:

*Length*.—22.50 mm.

*Width*.—19.33 mm.

*Weight*.—3.35-4 g/fruit.

*Shape*.—Conical.

*Number of drupelets*.—132 per fruit.

*Color of mature fruit*.—RHS 46A (Strong red).

*Color of mature fruit internal flesh*.—RHS 53A (Deep red).

*Receptacle*.—Depth: 12.19 mm. Width: 5.85 mm.

*Seed*.—Length: 2.30 mm. Width: 1.33 mm. Shape: Ovoid. Color: RHS 159C (Pale orange yellow).

Production:

*Floricane* (*previous year's cane*).—Time of vegetative bud burst: March. Time of beginning of flowering: Late April to May. Time of beginning of fruit ripening: June. Length of fruiting period: Mid-June to early August. Yield: 8,000 lbs-16,000 lbs of fruit per acre per season for 26-month-old plants grown in Whatcom County, Washington, U.S.A.

Resistance to abiotic stress, pests, and diseases:

*Heat*.—Fruit sunburn has been observed at temperatures exceeding 100° F. during fruit ripening.

*Cold*.—Injury to overwintering primocanes has been observed at temperatures below −6° F.

*Drought*.—Susceptible to prolonged drought.

*Powdery mildew* (*podosphaera macularis*).—Moderately susceptible.

*Phytophthora root rot* (*phytophthora sp.*).—Moderately resistant.

*Cane and fruit botrytis* (*botrytis cinerea*).—Moderately susceptible.

COMPARISONS TO PARENTAL AND REFERENCE RASPBERRY VARIETIES

'DrisRaspTwentyThree' differs from the proprietary female parent 'W678.2' in that fruit of 'DrisRaspTwentyThree' are more uniform in color and more red than fruit of 'W678.2'. Additionally, during machine harvest, fewer unripe green fruit of 'DrisRaspTwentyThree' are removed than in 'W678.2'.

'DrisRaspTwentyThree' differs from the male parent and reference variety 'Meeker' in that 'DrisRaspTwentyThree' has completely thornless canes and medium red fruit color, whereas 'Meeker' has thorny canes and dark red fruit color. Additionally, 'DrisRaspTwentyThree' has larger fruit than 'Meeker', and 'DrisRaspTwentyThree' begins bearing ripe fruit three to five days earlier than 'Meeker' when grown in Whatcom County, Washington.

'DrisRaspTwentyThree' differs from the reference raspberry variety 'Tulameen' (unpatented) in that 'DrisRaspTwentyThree' has absent or very weak anthocyanin coloration on current season's cane and spineless canes, whereas 'Tulameen' has weak anthocyanin coloration on current season's cane and spines present on canes.

What is claimed is:

1. A new and distinct variety of raspberry plant designated 'DrisRaspTwentyThree' as shown and described herein.

* * * * *